US006838993B2

(12) United States Patent
Beiswenger et al.

(10) Patent No.: US 6,838,993 B2
(45) Date of Patent: Jan. 4, 2005

(54) EARLY WARNING SYSTEM AND METHODS FOR DETECTION OF A BIOTERRORISM EVENT

(75) Inventors: John L. Beiswenger, Strasburg, PA (US); Michael H. Ranck, Strasburg, PA (US); Jody L. Taualofai, Lancaster, PA (US)

(73) Assignee: Bioalert Systems, Inc., Wilmington, DE (US)

( * ) Notice: Subject to any disclaimer, the term of this patent is extended or adjusted under 35 U.S.C. 154(b) by 468 days.

(21) Appl. No.: 10/080,746

(22) Filed: Feb. 22, 2002

(65) Prior Publication Data

US 2004/0116821 A1 Jun. 17, 2004

(51) Int. Cl.[7] .............................................. G08B 23/00
(52) U.S. Cl. ............................... 340/573.5; 340/573.1; 435/6
(58) Field of Search ......................... 340/573.1, 573.5, 340/573.7, 578, 584, 587, 588, 589; 382/115, 125; 607/101, 102, 108; 435/6

(56) References Cited

U.S. PATENT DOCUMENTS

| | | | | |
|---|---|---|---|---|
| 4,386,604 A | | 6/1983 | Hershey ..................... 128/718 |
| 5,370,122 A | | 12/1994 | Kunig et al. ................ 128/670 |
| 5,371,673 A | | 12/1994 | Fan ........................ 364/419.01 |
| 5,634,461 A | | 6/1997 | Faithfull et al. ............ 128/637 |
| 5,664,109 A | | 9/1997 | Johnson et al. ................ 705/2 |
| 5,826,214 A | | 10/1998 | Lieb et al. .................... 702/24 |
| 5,895,922 A | * | 4/1999 | Ho ......................... 250/492.1 |
| 6,030,342 A | | 2/2000 | Amano et al. ............. 600/301 |
| 6,051,189 A | * | 4/2000 | Wick et al. .............. 422/82.01 |
| 6,059,724 A | | 5/2000 | Campell et al. ............ 600/300 |
| 6,173,068 B1 | * | 1/2001 | Prokoski ..................... 382/115 |
| 6,193,654 B1 | | 2/2001 | Richardson et al. ........ 600/300 |
| 6,278,999 B1 | | 8/2001 | Knapp ........................... 707/9 |
| 6,298,328 B1 | | 10/2001 | Healy et al. .................. 705/10 |
| 6,316,197 B1 | | 11/2001 | Das et al. ....................... 435/6 |
| 6,317,080 B1 | | 11/2001 | Baxter, Jr. ............. 342/357.09 |
| 6,448,016 B1 | * | 9/2002 | Rastogi et al. .................. 435/6 |
| 6,470,216 B1 | * | 10/2002 | Knowlton ................... 607/101 |
| 6,498,041 B1 | * | 12/2002 | Tabacco et al. ............. 436/172 |
| 6,569,630 B1 | * | 5/2003 | Vivekananda et al. ......... 435/6 |
| 6,694,799 B2 | * | 2/2004 | Small ........................ 73/24.02 |
| 2001/0041991 A1 | | 11/2001 | Segal et al. ..................... 705/3 |
| 2002/0016553 A1 | | 2/2002 | Tamaki et al. .............. 600/549 |

OTHER PUBLICATIONS

"Bioterrorism: A Public Health Issue," *Missouri Epidemiologist*, vol. 21, No. 5, Sep.–Oct. 1999.
The Journal of the American Medical Association, Wendy A. Weiger; Mark E. Shaw; John S. Edelsberg; James M. Chamberlain; Thomas E. Terndrup; David Alexander; Sue Binkley; Richard Opiekun; Gail S. Marion; Patricia K. McGann; David H. Walworth; Philip A. Mackowiak; Steven S. Wasserman; Myron M. Levine, JAMA, V269, N10, P1249, Mar. 10, 1993.
BBTThermometer. http://web.archive.org/web/20010417220224/http://www.asklynnrn.com, Mar. 20, 2001.
Confronting Smallpox: Bioterrorism Threat is Real., Maureen Habel, MA, RN, and Pat Metcalf, MA, RN., http://nurseweek.com/ce/ce101a.html, Dec. 17, 2001.
Hospital Internet System Could Spot Bioterrorist Attack., http://web.mit.edu/hi=st.921/www/IEEE.htm, Dec. 17, 2001.

* cited by examiner

*Primary Examiner*—Van T. Trieu
(74) *Attorney, Agent, or Firm*—Womble Carlyle Sandridge & Rice, PLLC

(57) ABSTRACT

A method and system for an early warning detection of bioterrorism events includes obtaining temperature readings from a statistical sample of individuals in a community, and comparing the individual readings to one or more detection thresholds spaced apart by predetermined values with at least one of the thresholds being below the normally accepted temperature range defined as a low-grade fever. The comparison is then used to identify and evaluate a community's potential infection by a biological warfare agent so that early therapeutic action may be taken.

86 Claims, 13 Drawing Sheets

Figure 1A:
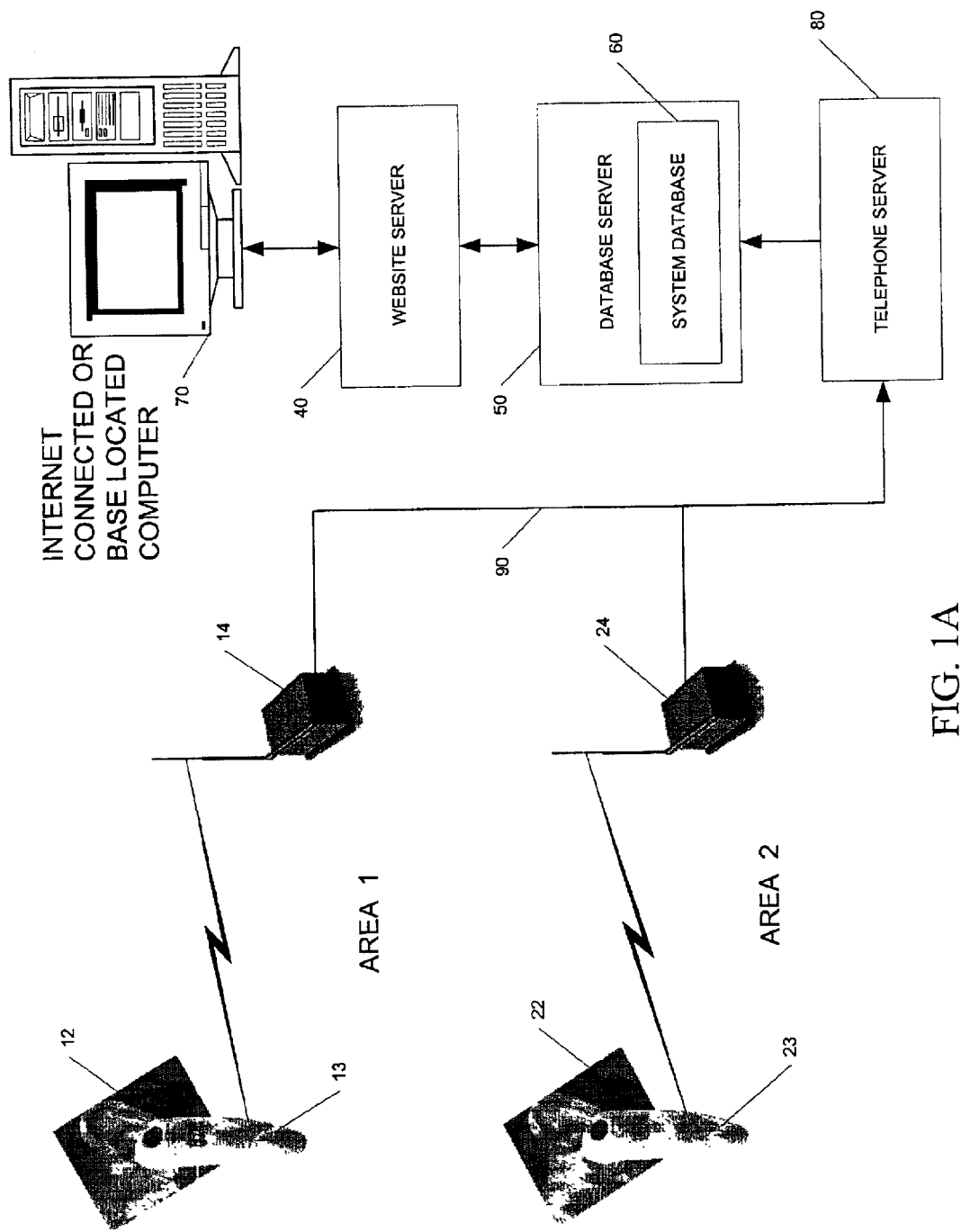

ENTER YOUR GRAPHCHART ID:

ENTER YOUR FOUR DIGIT PIN:

ENTER YOUR BMT READING

CHECK THE BOX IF, WITHIN THE LAST 24 HOURS YOU:

ATTENDED A GATHERING OF MORE THAN 500   ⊙ NO ○ YES

EXPERIENCED SYMPTOMS OF A COLD, THE FLU OR A SORE THROAT   ⊙ NO ○ YES

RECEIVED A CURRENT FLU SHOT   ⊙ NO ○ YES

ENTER YOUR BIO-WATCH ID:

FIG. 2

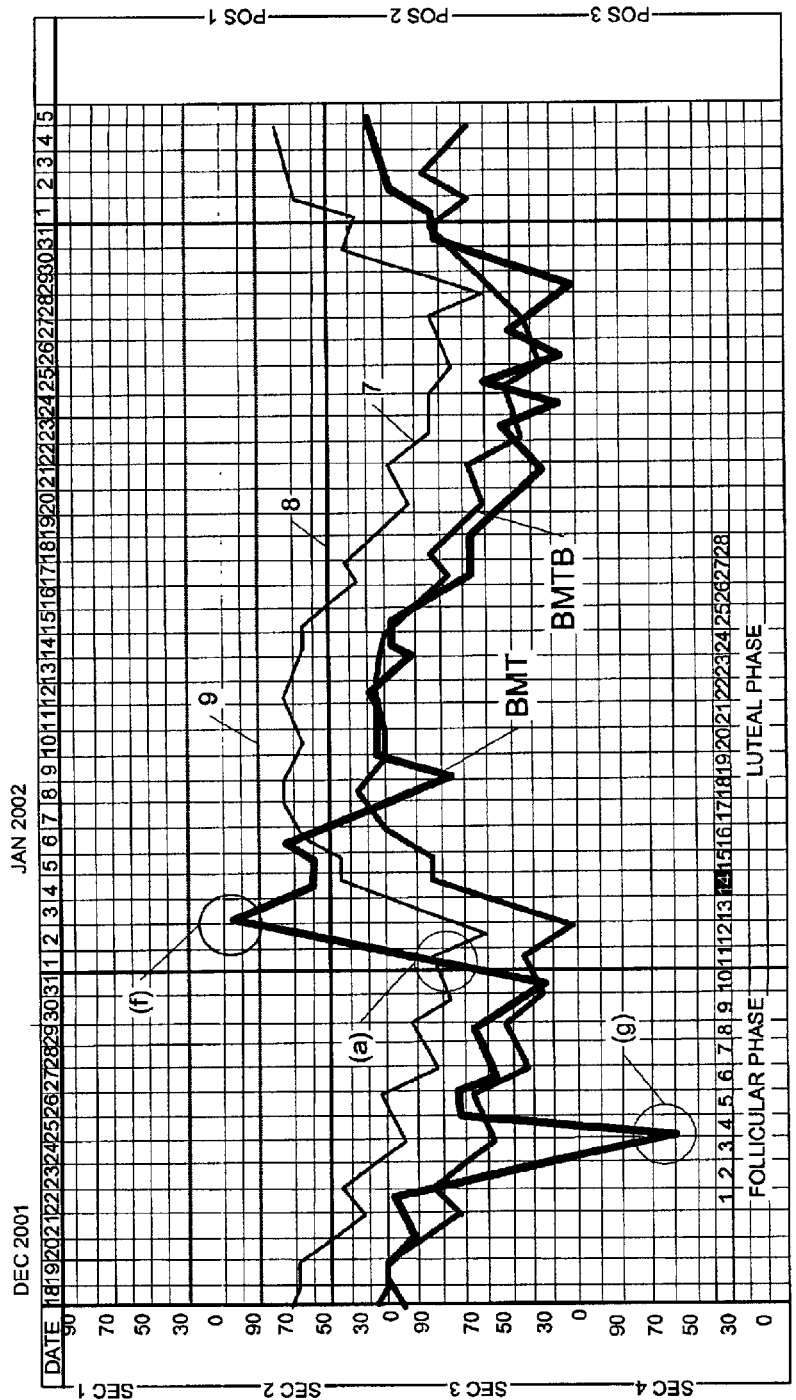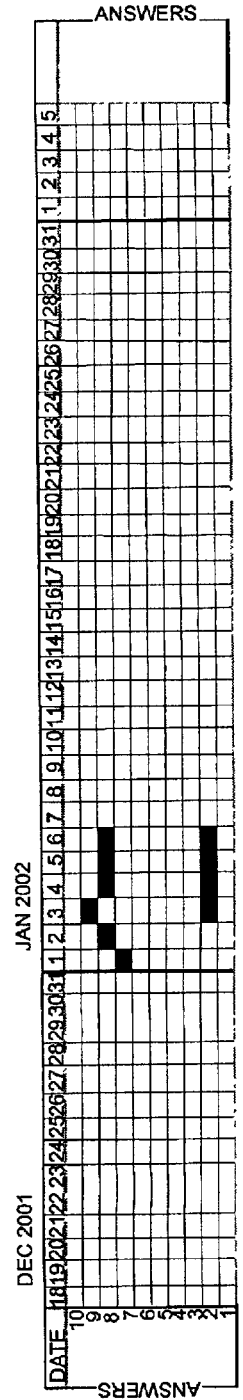
FIG. 3
FIG. 4

EARLY WARNING SYSTEM AND METHODS FOR DETECTION OF A BIOTERRORISM EVENT

BACKGROUND OF THE INVENTION

The present invention is generally related to healthcare monitoring systems. More particularly, the present invention is directed to the detection of infectious diseases in individuals or communities.

Bioterrorism is the use of biological agents to intentionally produce disease in unsuspecting and susceptible individuals or populations. Bioterrorism has become an increasing concern throughout the world, and particularly in the United States. While still requiring a high level of expertise and financial resources, advances in biotechnology have made the production and dissemination of pathogenic organisms or chemical toxins a real threat. Because of this significant threat, it is of paramount importance for the government, public health community, and the medical profession to be prepared for this type of health emergency.

Early detection of a bioterrorism attack is crucial. Some biological agents cause diseases that have relatively short incubation periods, and have high mortality rates when proper treatment is not initiated early in the course of infection. For biological agents that can be transmitted from person-to-person, it is even more crucial to identify the disease early. The Centers for Disease Control and Prevention (CDC) has listed as Category A (high-priority agents include organisms that pose a risk to national security) many potential agents including *Bacillus anthracis* (anthrax), variola major virus (smallpox), *Yersinia pestis* (pneumonic plague), filovirus (Ebola hemorrhagic fever), filovirus (Marburg hemorrhagic fever), Lassa—arena virus (Lassa fever), Junin—arena virus (Argentine hemorrhagic fever) and *Francisella tularensis* (tularemia). Identification of these agents is difficult because they are not expected, and most healthcare providers are not familiar with them. All of the above present symptoms that include fevers.

Human anthrax has three major clinical forms: cutaneous, gastrointestinal, and inhalation. Cutaneous anthrax is a result of introduction of a spore through the skin. Gastrointestinal anthrax is a result of the introduction of a spore by ingestion. Inhalation anthrax is a result of introduction of a spore through the respiratory tract. After an incubation period, inhalation anthrax presents as fever, malaise, fatigue, cough, mild chest discomfort and possibly vomiting and abdominal pain. This stage can last for hours or days. In untreated patients, there may or may not be a period of improvement. The patient then abruptly develops severe respiratory distress with dyspnea, diaphoresis, stridor, and cyanosis. Shock and death occur within 24–36 hours after the onset of severe symptoms. Case fatality rates for inhalation anthrax are thought to approach 90–100%.

From Oct. 4 to Nov. 2, 2001, the first ten confirmed cases of inhalation anthrax caused by intentional release of *Bacillus anthracis* ("*B. anthracis*") were identified in the United States. Epidemiological investigation indicated that the outbreak, in the District of Columbia, Florida, New Jersey, and New York, resulted from intentional delivery of *B. anthracis* spores through mailed letters or packages. The median age of patients was 56 years, 70% were male. The median incubation from the time of exposure to onset of symptoms, when known, was four days. Symptoms at initial presentation included fever or chills, sweats, fatigue or malaise, minimal or non-productive cough, dyspnea, and nausea or vomiting. The median white blood cell count was $9.8 \times 10^3/mm^3$.

Smallpox was declared eradicated by the World Health Organization in 1980. Two repositories were approved to hold the remaining variola major virus. These two reference laboratories are the CDC in Atlanta, Ga., and a laboratory in Moscow. During the past several years, accusations have been made that the smallpox virus was weaponized in the Soviet Union, and there is concern that virus stores may have been moved to additional sites. Routine vaccination for smallpox in the United States was discontinued among civilians in 1972. The immune status of individuals vaccinated before that time is not certain, but immunity is believed to decline substantially within ten years of vaccination. Therefore, there is a high susceptibility to this infection world-wide. Smallpox transmission is person-to-person by respiratory discharges, by direct contact with skin lesions, or contact with contaminated bedding or clothing. The incubation period averages 12–14 days, with the range being 7–17 days. Individuals are not infectious until the onset of a rash. Smallpox infection begins with an abrupt onset of fever, malaise, rigors, vomiting, headache, and backache. Lesions appear 2–3 days later. Mortality is approximately 30%; death is thought to occur from toxemia associated with circulating immune complexes and soluble variola major antigens.

If a bioterrorism event, such as the release of a Class A biological warfare agent upon a populated area, can be detected before infected persons experience initial symptoms, which include low-grade fevers (defined as 100 to 102 degrees Fahrenheit), 90 percent of the infected individuals can be saved. Yet, the only existing detection systems in place in the U.S. rely on activity reports from emergency medical services, hospitals, clinics, physicians, epidemiologists and coroners. In other words, there is no detection system in place that alerts health officials before individuals experience initial symptoms.

Various electronic detectors for a variety of biological warfare agents have been and are being developed. The obvious questions with these are where to place them and how many will be needed to be effective? Biological warfare agents are targeted to kill people wherever they gather, such as in homes, schools, malls, stadiums, factories, offices, churches, gymnasiums, public buildings, retail stores, postal facilities, government buildings, hospitals, restaurants, entertainment facilities and city streets. People gather in small and large groups, and at different times and at different places. Electronic detectors cannot possibly be positioned everywhere people might gather.

SUMMARY OF THE INVENTION

The present invention is directed to an early warning detection system that monitors the basal metabolic temperature (BMT) data from a statistical number of individuals in a given population. The monitoring of individuals serves as logically placed "sensors," since they are positioned, by definition, wherever people are gathered.

Basal metabolic rate ("BMR") is the rate of metabolism (chemical activity) required to maintain life when an individual is at digestive, physical and emotional rest. BMT is the resulting core body temperature. A sufficiently accurate BMT can be obtained immediately upon wakening after a reasonable period of sleep, preferably six to eight hours. BMT can be measured with a basal thermometer. An above normal BMT can mean the presence of an infectious process. A below normal BMT may occur prior to the above-normal reading. The BMT of an individual may rise 24–48 hours prior to the individual experiencing any symptoms of an infectious disease. Class A biological warfare agents, such as anthrax and smallpox, cause an immune response increasing the rate of metabolism above the individual's normal BMR as evidenced by an increase in temperature above the individual's normal BMT.

When monitoring the BMT data from a statistical number of individuals in a given population, factors associated with normally occurring diseases can be considered by comparing the average readings of other populations, e.g., comparing readings from the population in one zip code with the readings from a population in another zip code. Gross differences would give an indication of an infectious disease in the zip code area with higher numbers of above normal BMT readings. In addition, the suddenness of widespread changes in BMT readings exceeding established thresholds and coming from a specific area, would immediately alert health officials that a bioterrorism event has occurred affecting that area.

There are many factors that can affect the BMT of an individual. Fluctuations occur due to the body's cyclical changes. For women, some of these fluctuations are connected to the reproductive hormones. Prior to ovulation, BMT for women ranges from approximately 97.0° F. to 97.5° F. The BMT rises between approximately 0.4° F. and 0.8° F. on the day of ovulation. During the post ovulatory (luteal) phase of the cycle, the hormone progesterone is released, which elevates the BMT. Monitoring BMT data without taking into consideration cyclical changes may result in the report of many false positives.

The invention includes several algorithms, for producing basal metabolic temperature baselines (BMTB) for individuals, which take into consideration cyclical fluctuations. The algorithms also produce one or more detection thresholds. The algorithms are used to increase detection sensitivity while they reduce false positive results.

Another aspect of the invention involves (i) monitoring an individual's BMT, (ii) observing BMT changes that exceed detection thresholds, (iii) receiving a throat swab test for influenza, and if negative, (iv) receiving a blood test for biological warfare agents, thereby providing a method for an affected individual to take lifesaving action in the event of an individual attack.

Furthermore, the invention includes a health monitoring system to (i) obtain BMT readings from a statistical sample of individuals in a community, and (ii) compare the individual readings to one or more detection thresholds for the purpose of identifying and evaluating a community's potential infection by a biological warfare agent so that early therapeutic action may be taken.

DESCRIPTION OF THE DRAWINGS

The invention is better understood by reading the following detailed description of an exemplary embodiment in conjunction with the accompanying drawings.

FIG. 1A illustrates an exemplary embodiment of the architecture of the early warning detection system of the present invention. FIG. 1B illustrates an Internet-based embodiment of the architecture of the early warning detection system.

FIG. 2 illustrates a data entry user interface for an individual to input basal metabolic temperature (BMT) to the early warning detection system over a secure web page.

FIG. 3 illustrates the BMT graph of a pre-menopausal female, corresponding detection threshold values, and the indication of a biological event such as a cold or the flu, in accordance with an exemplary embodiment of the present invention.

FIG. 4 illustrates a chart indicating an individual's response to the questions illustrated on FIG. 2 and indicating detection thresholds exceeded on given days, in accordance with an exemplary embodiment of the invention.

FIG. 5 illustrates a graphical comparison of the relative rise in average basal metabolic temperatures over a period of time from infection by a biological warfare agent and infection by an influenza virus in accordance with an exemplary embodiment of the present invention.

FIG. 6 illustrates a chart indicating average basal metabolic temperature averages that exceed detection threshold values for residents of specific zip code areas in accordance with an exemplary embodiment of the invention.

FIG. 7 illustrates a chart indicating basal metabolic temperature averages that exceed the various detection threshold values in any prespecified area in accordance with an exemplary embodiment of the invention.

FIG. 8 illustrates a chart indicating absolute numbers and percentages of participants having basal metabolic temperatures that exceed the various detection threshold values in accordance with an exemplary embodiment of the invention.

FIG. 9 illustrates the BMT data graph of a pre-menopausal female.

FIG. 10A illustrates the BMT data graph of FIG. 9 after the data has been processed by Algorithm I in accordance with an exemplary embodiment of the present invention.

FIG. 10B illustrates the BMT data graph of FIG. 9 after the data has been processed by Algorithm II in accordance with an exemplary embodiment of the present invention.

FIG. 10C illustrates the BMT data graph of FIG. 9 after the data has been processed by Algorithm III in accordance with an exemplary embodiment of the present invention.

FIG. 11 illustrates a representative BMT data graph of a male after the date has been processed by Algorithm I in accordance with an exemplary embodiment of the present invention.

DETAILED DESCRIPTION OF THE INVENTION

The present invention is directed to an early warning system and methods for detection of bioterrorism events and provides (i) a method to detect a bioterrorism event before infected persons experience initial symptoms including low-grade fevers (i.e., 100° F. to 102° F.) and (ii) a method to detect a bioterrorism event wherever people gather. The early warning system is provided through a data monitoring system as more fully described herein.

Basal metabolic rate (BMR) is the rate of metabolism (chemical activity) required to maintain life when an individual is at digestive, physical and emotional rest. Basal body temperature, also referred to interchangeably herein as basal metabolic temperature (BMT) is the resulting core body temperature. A sufficiently accurate BMT can be obtained immediately upon waking after a reasonable period of sleep, preferably six to eight hours.

To obtain an accurate BMT, a digital basal thermometer should be used since it is ultra sensitive in measuring the body's exact temperature. A normal fever thermometer should not be used since it does not produce the accuracy or range needed. Generally, the BMT reading should be taken at close to the same time daily upon wakening.

FIG. 1A illustrates an exemplary embodiment of the system architecture of the early warning detection system. The figure shows a website server 40, along with associated database server 50 and a database 60. The database 60 stores current and historical information for a plurality of participants in the early warning detection system. For simplicity, the figure shows participants 12 in a first area (Area 1) and participants 22 in a second area (Area 2). The individual participants (12 and 22) take their BMT with infrared ear type thermometers 13 and 23 respectively (requiring less than two seconds). The BMT data is subsequently and automatically transmitted by means of a wireless transmitter within the thermometer to receiver 14 in Area 1 and receiver 24 in Area 2. Multiple wireless thermometers can interface with any receivers within reception range (approximately 150 feet). Once the data is acquired by the receivers it is forwarded by means of telephone network 90 to the early warning system telephone server 80 capable of connecting to multiple incoming telephone lines. The telephone server 80 forwards the data to the database server 50, which adds the data to database 60. Early warning system administrators can access the website server 40 and thereby the database server 50 and database 60 from individual personal computers 70, laptops, personal digital assistants (PDAs), workstations, etc. via a dial-up connection or dedicated connection over the Internet. Any common networking configuration is suitable including through local area networks (LANs), virtual private networks (VPNs) and the like. Although a single system (defined by the telephone server 80, database server 50, database 60 and website server 40) is shown, the invention contemplates the use of multiple systems to support regional, multi-state and national coverage with interlinked databases. The invention is highly scaleable in this regard.

Figure 1B:
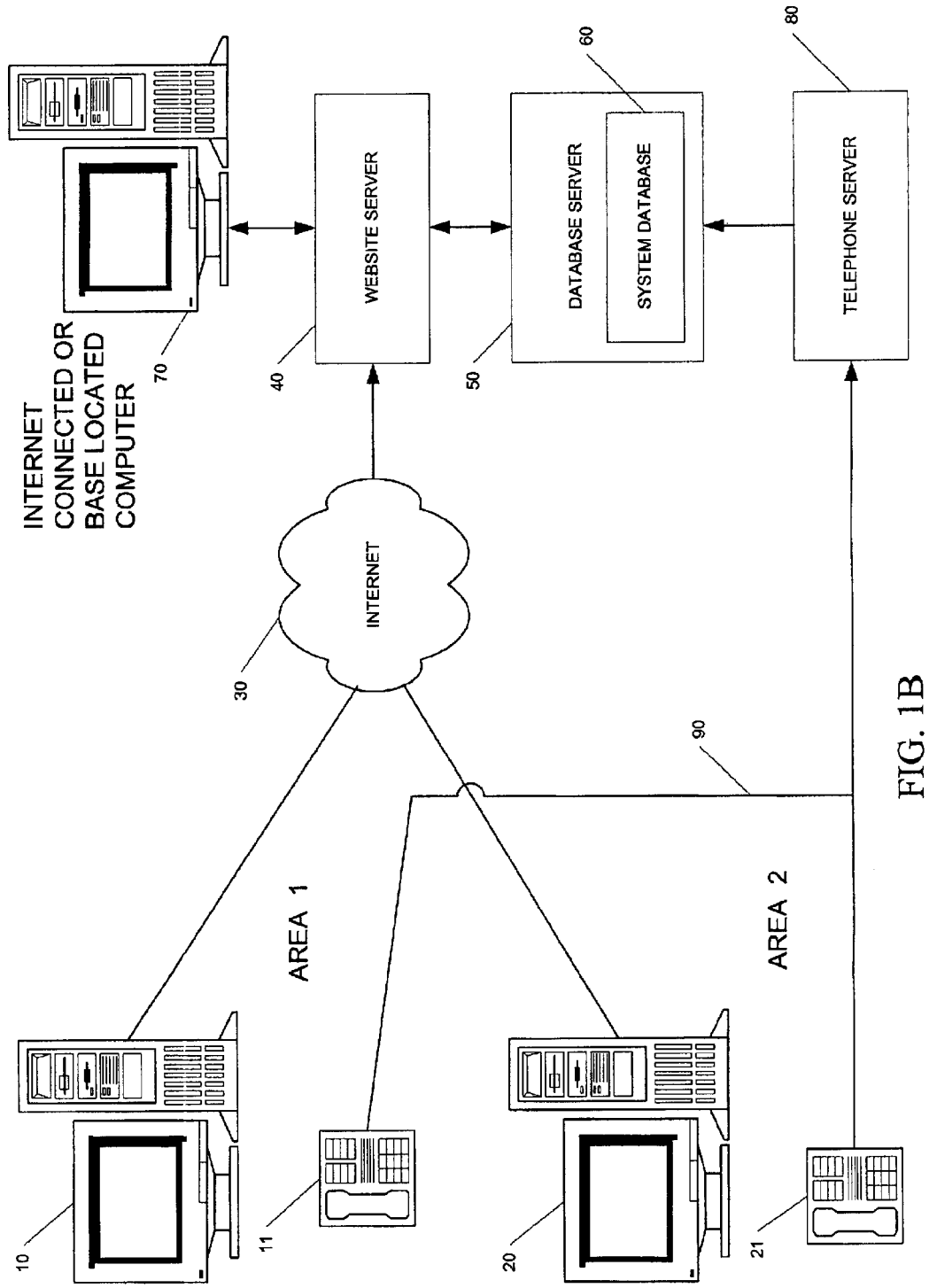

FIG. 1B illustrates an Internet-based embodiment of the system architecture of the early warning detection system. The figure shows a website server 40, along with associated database server 50 and a database 60. The database 60 stores current and historical information for a plurality of participants in the early warning detection system. For simplicity, the figure shows participants 10, 11 in a first area (Area 1) and participants 20, 21 in a second area (Area 2). The individual participants 10, 20 can access the website server from individual personal computers, laptops, PDAs, workstations, etc. via a dial-up connection or dedicated connection over the Internet 30 through an Internet Service Provider (ISP—not shown). Any common networking configuration is suitable including through LANs, VPNs and the like. Communications between participants 11, 21 and the early warning system can take place over telephone network 90 by means of conventional or cellular phones using a menu-driven interface. Communications between participants 10, 20 and the website can also be wireless through a wireless service provider or even satellite Internet services. Early warning system administrators can access the website server 40 and thereby the database server 50 and database 60 from individual personal computers 70, laptops, PDAs, workstations, etc. via a dial-up connection or dedicated connection over the Internet. Any common networking configuration is suitable including through LANs, VPNs and the like. Although a single system (defined by the telephone server 80, database server 50, database 60 and website server 40) is shown, the invention contemplates the use of multiple systems to support regional, multi-state and national coverage with interlinked databases. The invention is highly scaleable in this regard.

Once a registered participant of the data monitoring system takes his or her temperature, the participant reports it to the early warning system either using a touch-tone telephone via keypad date entry, or via the early warning system's Internet data entry site. The early warning system administrator in this context can be a federal agency, a state agency, or a telehealthcare company, such as the assignee of the present invention. FIG. 2 illustrates an online data entry form that can be used with the present invention by individuals 10, 20. The website server may provide a secure communications connection to enable individuals to access their own BMT graphs by entering their unique system ID number and personal identification number (PIN). The lower portion of FIG. 2 enables the individuals to indicate if a change in circumstances has occurred, such as exposure to a gathering of more than 500 people, development of flu-like symptoms, or having received a current flu shot. These events will be important to early warning system administrators during analysis of the data.

Soon after most biological warfare agents enter the body there is an immune system response increasing the rate of metabolism above the individual's normal BMR as evidenced by an increase in temperature above the individual's normal BMT (above normal BMT defines $BMT^\Delta$ or BMT Delta). The BMT of an infected individual will rise above his or her normal BMT up to 48 hours before initial symptoms of the infection are experienced.

Therefore, early detection of a bioterrorism event can be achieved by monitoring the BMT data from a statistically significant number of individuals in any given population. The monitored individuals serve as the "sensors" that are, of course, positioned wherever people gather. However, many factors can effect the BMT of an individual. These include (i) normal monthly (approximately 28 day) cyclical changes that occur in the human body and (ii) non-cyclical changes, such as variations in one's sleep, food, drink, exercise, and stress (both physical and emotional) that may have occurred within the previous 24 hours. Therefore, monitoring unprocessed BMT data will tend to cause multiple false-positive reports. To reduce false-positive reports, several algorithms have been developed. The algorithms described below produce Basal Metabolic Temperature Baselines (BMTB™) for individuals, which take into consideration cyclical and recurring non-cyclical changes.

The algorithms progressively increase the sensitivity of the early warning system while reducing false-positive reports. The algorithms produce detection thresholds for individuals. Detection thresholds are temperature values spaced by predetermined values whereby at least one of the detection thresholds is below the normally accepted temperature range defined as "low-grade fever." Processing BMT data, using these detection threshold algorithms, progressively increases the sensitivity of the early warning system while reducing false-positive reports. The early warning system will indicate the number of individuals in a given area with BMT readings above each detection threshold (see FIGS. 6, 7, 8). FIG. 9 illustrates the BMT data graph of a pre-menopausal female. The heavy-line curve is the actual graphed BMT data submitted by a participant. The thin-line curve represents the typical curve expected by graphing the BMT data of a pre-menopausal female. Three points on the actual curve are circled. Point (a) indicates an event occurred on that day which should be detected by the early warning system as a possible infection. Point (b) indicates a drop in progesterone probably due to poor capacitation of the corpus luteum (yellow body) developed during the follicular phase (F). Point (c) is a normal point on the luteal phase of the curve the significance of which will be explained later. Point (d) is a meaningless spike in the BMT data, which occurred during the luteal phase (L).

Figure 9:
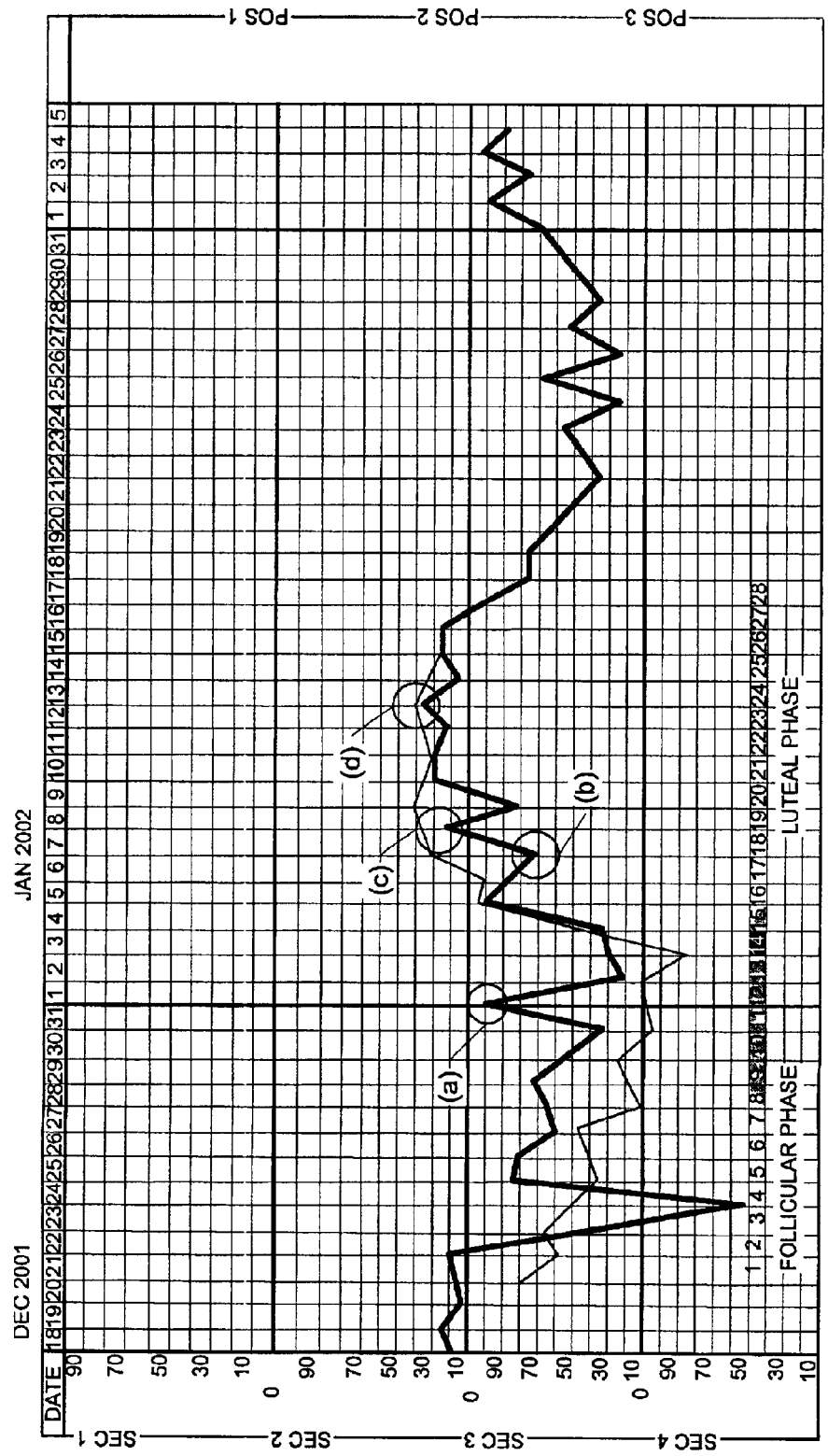
Figure 10A:
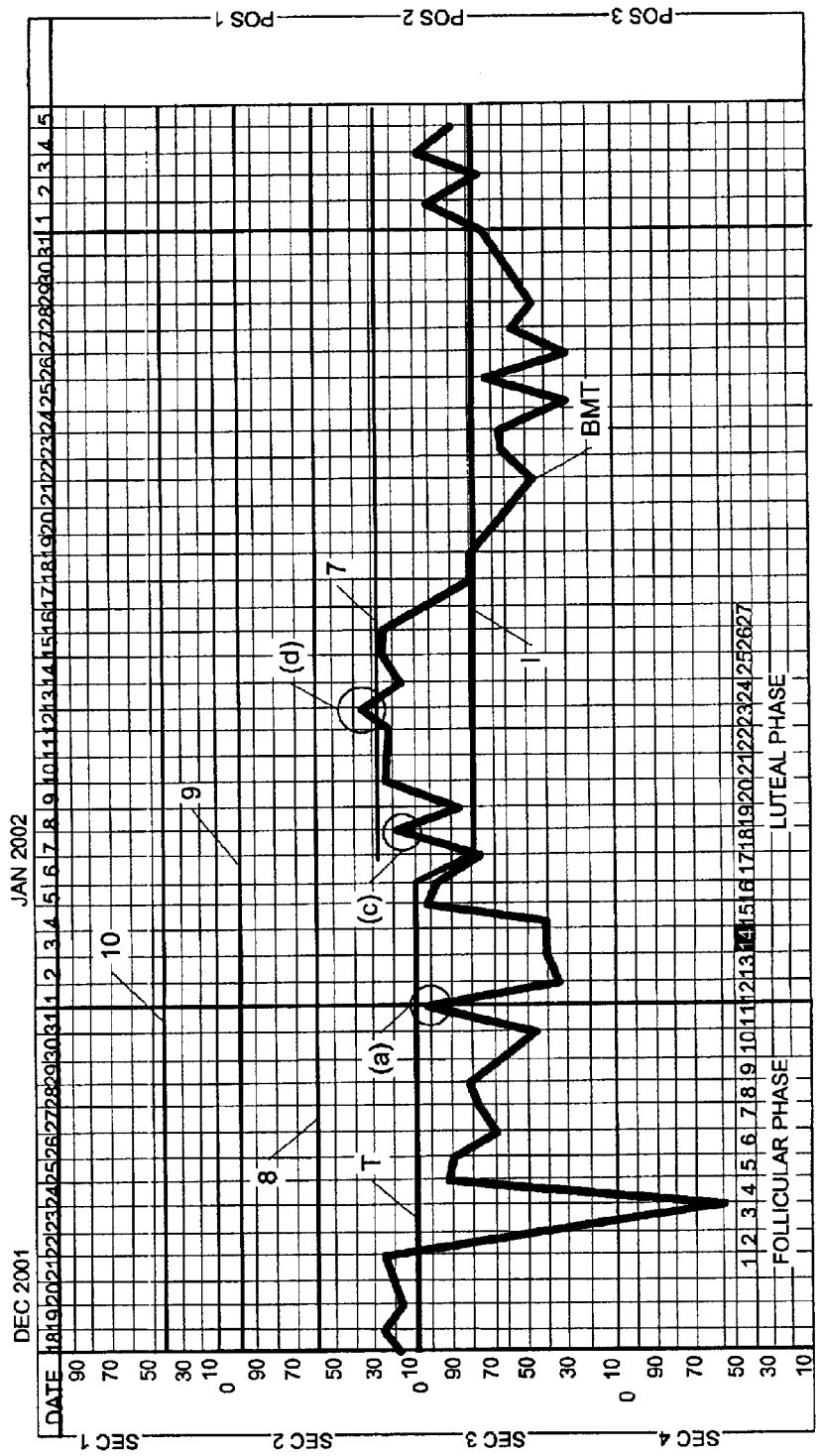

FIG. 10A illustrates the BMT data graph of FIG. 9 after the data has been processed by Algorithm I. Algorithm I produces three fixed detection thresholds illustrated on line 30 of Sec. 1 (detection threshold 10), line 90 of Sec. 2 (detection threshold 9) and line 50 of Sec. 3 (detection threshold 8). The detection thresholds are spaced apart by a predetermined number of tenths of a degree F. and the lowest threshold at line 50 of Sec. 2 is spaced by a predetermined number of tenths of a degree F. above "T" illustrated on line 00 between Sec. 2 and 3. During the first 30 days, a fixed value ("T") is used as an average BMT value while Algorithm I develops "I," the actual average BMT of the individual. Once "I" is determined, Algorithm I adds an additional, lower threshold (detection threshold 7). The addition of detection threshold 7 increases the sensitivity of the early warning system by adding a detection threshold that is lower than the lowest fixed detection threshold 8. Algorithm I enables the early warning system to be somewhat more responsive to the participant's BMT data by referencing the individual's actual BMT average "I." Therefore, the early warning system is immediately effective in monitoring $BMT^A$ due to the fixed detection thresholds Algorithm I establishes and it becomes more sensitive after the BMT average is based on "I" values. Note in FIG. 10A that, applying Algorithm I, meaningless point (d) would have been detected by detection threshold 7 as an event, while the actual event point (a) would not.

Figure 10B:
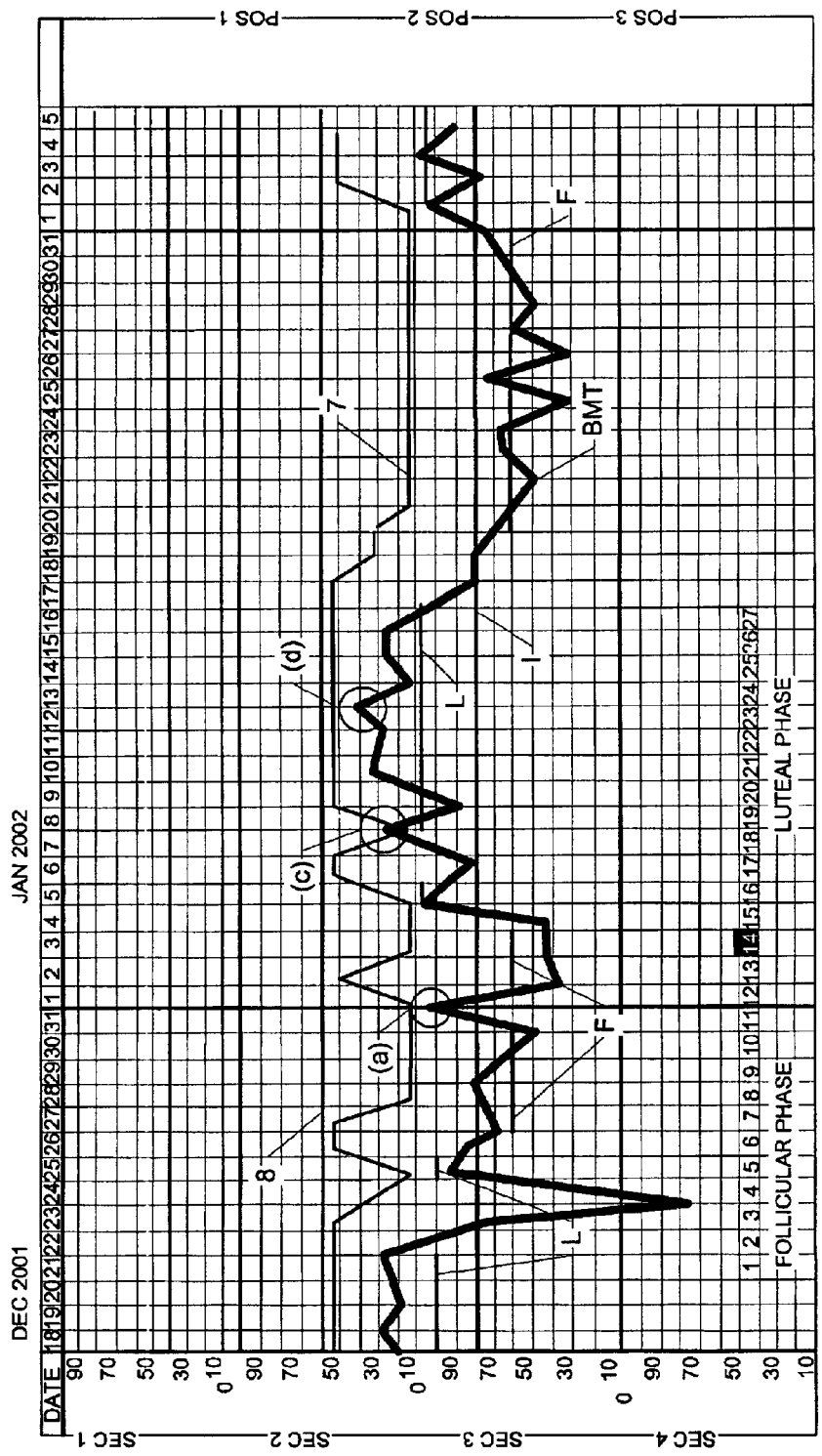

FIG. 10B illustrates the BMT data graph of FIG. 9 after the data has been processed by Algorithm II. Algorithm II can be introduced subsequent to Algorithm I, i.e., after approximately 30 days of data is received from an individual and "I" is established. Algorithm II averages BMT values that are below "I," producing a value referred to as "F," and those that are above "I," producing a value referred to as "L." Algorithm II thereby modifies detection threshold 7, which is now based on "F" and "L." Therefore, Algorithm II causes the early warning system to become effectively cycle-responsive, while it increases the sensitivity of the early warning system. Note in FIG. 10B that, applying Algorithm II, meaningless point (d) would not have been detected by detection threshold 7 as an event, normal point (c) would have been detected as an event, while the actual event point (a) would not have been detected as an event.

Figure 10C:
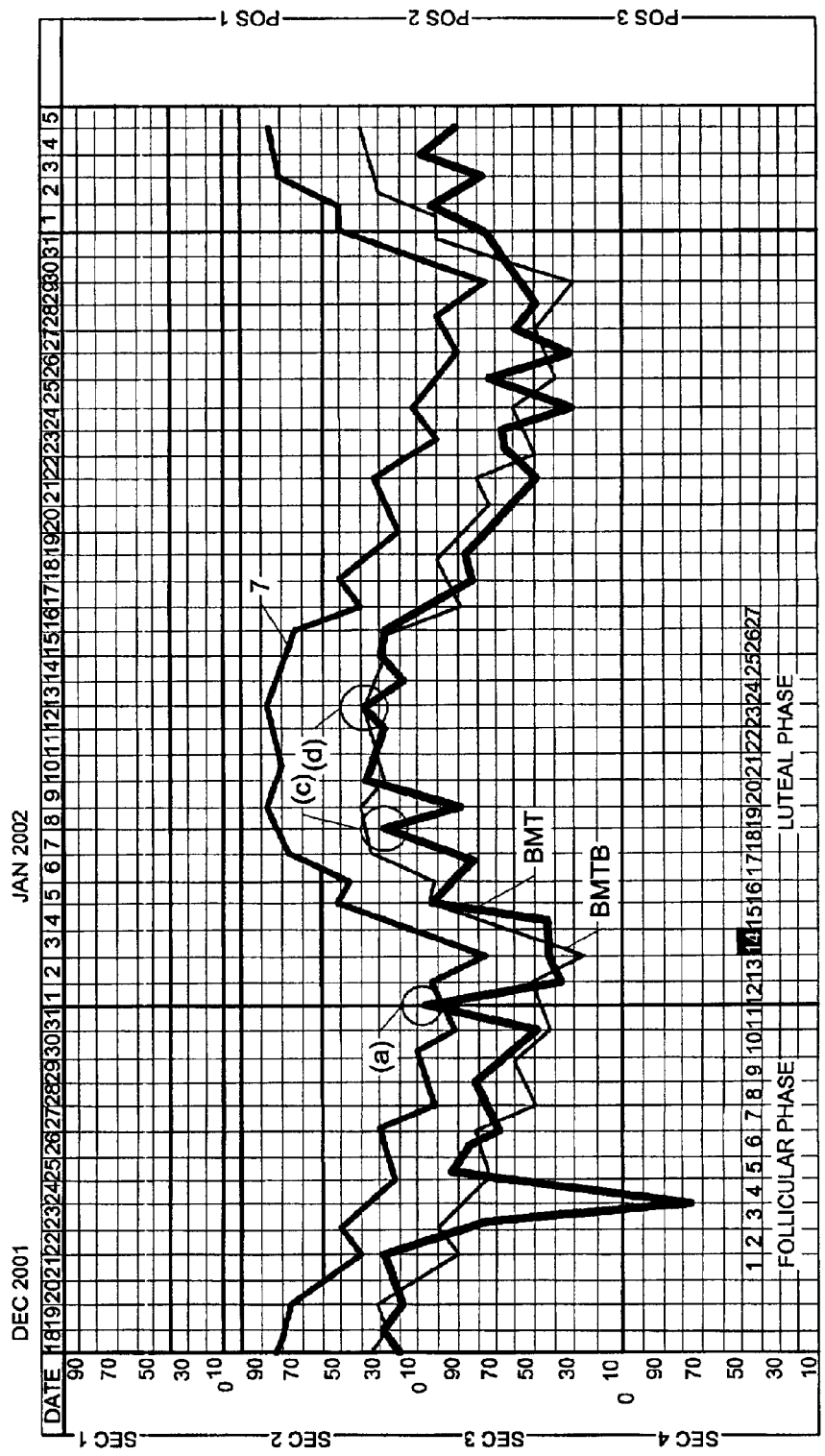

FIG. 10C illustrates the BMT data graph of FIG. 9 after the data has been processed by Algorithm III. Algorithm III can be introduced subsequent to Algorithm II, i.e., after approximately 30 additional days of data is received from an individual and "F" and "L" are established. Algorithm III recognizes the cyclical nature, if any, of the BMT data from the repeating monthly "switch-over" from "F" to "L" and thereby establishes a starting point for an individual's monthly (approximately 28 day) cycle. Algorithm III averages the BMT data of each day of the cycle with the BMT data of the same day of the previous cycle and thereby produces an accurate, fully responsive BMTB and modifies detection threshold 7, which farther increase the sensitivity of the early warning system while reducing false-positive reports as illustrated in FIG. 10C. Note in FIG. 10C that detection threshold 8 has been modified to correspond to, and in some places eliminate, detection threshold 7. Note also in FIG. 10C that, applying Algorithm III, meaningless point (d) would not have been detected by detection threshold 7 as an event, normal point (c) would not have been detected as an event and the actual event point (a) would have been detected.

Figure 11:
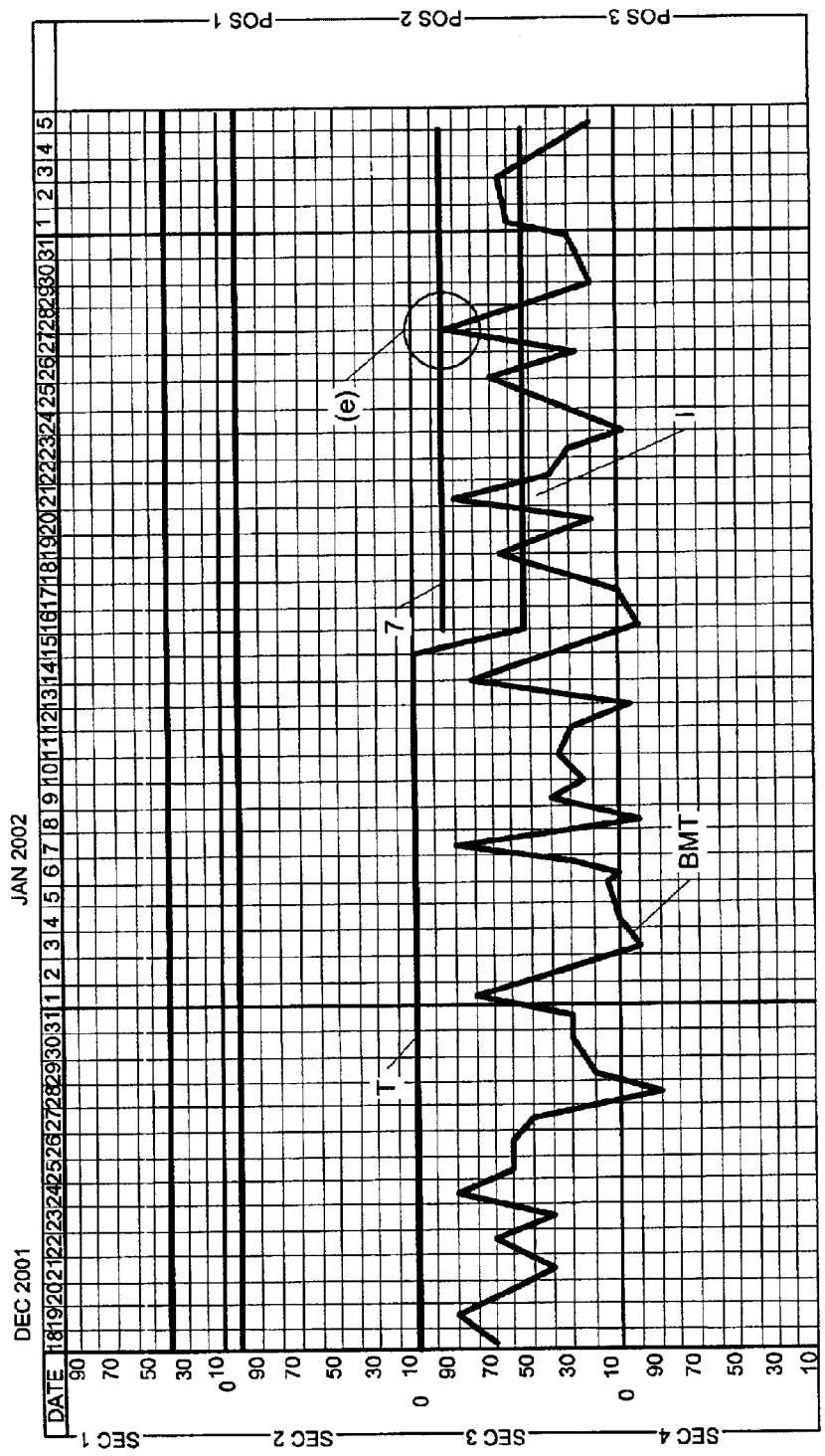

FIG. 11 illustrates a representative BMT data graph of a male. FIG. 11 illustrates the BMT data graph of FIG. 9 after the data has been processed by Algorithm I. Algorithm I produces three fixed detection thresholds illustrated on line 30 of Sec. 1 (detection threshold 10), line 90 of Sec. 2 (detection threshold 9) and line 50 of Sec. 3 (detection threshold 8). The detection thresholds are spaced by a predetermined number of tenths of a degree F. and the lowest threshold at line 50 of Sec. 2 is spaced by a predetermined number of tenths of a degree F. above "T" illustrated on line 00 between Sec. 2 and 3. During the first 30 days, a fixed value ("T") is used as an average BMT value while Algorithm I develops "I," the actual average BMT of the individual. Once "I" is determined, Algorithm I adds an additional, lower threshold (detection threshold 7). The addition of detection threshold 7 increases the sensitivity of the early warning system by adding a detection threshold that is lower than the lowest fixed detection threshold 8. Algorithm I enables the early warning system to be somewhat more responsive to the participant's BMT data by referencing the individual's actual BMT average "I." Therefore, the early warning system is immediately effective in monitoring $BMT^A$ due to the fixed detection thresholds Algorithm I establishes and it becomes more sensitive after the BMT average is based on "I" values. Note in FIG. 11 that, applying Algorithm I, meaningless point (e) would have been detected by detection threshold 7 as an event.

FIG. 3 illustrates the BMT data of FIG. 10C except that it also illustrates what might have occurred if the actual event point (a) had developed into a brief illness. Detection threshold 7 reported the event on January 1, as illustrated in FIG. 4. On January 2, detection threshold 8 reported the increase in BMT. It was not until January 3 that the individual reported cold/flu symptoms (by answering YES to question 2 on the user interface display of FIG. 2). Detection threshold 9 was triggered when she reported a temperature of almost 99.0° F. point (f), still below a low-grade fever (100° F. to 102° F.). The impending fever was possibly controlled by the individual with medication on the following days, but her metabolic rate was still high enough to trigger detection threshold 8 for the three remaining days that she reported experiencing cold/flu symptoms. As a matter of reference, point (g) indicates that the individual experienced a below normal BMT seven days before point (a) was recorded.

As discussed above, there are, of course, causal factors for $BMT^A$ readings other than bioterrorism events, such as, normally occurring diseases like the common cold, sore throat or influenza. When monitoring the BMTs of a statistical number of individuals in a given population, these factors can be considered by comparing the average readings of other populations (e.g., comparing readings from one ZIP code with those of another). The suddenness of widespread $BMT^A$ readings, that exceed BMTB thresholds, coming from a specific area would immediately alert health officials that a bioterrorism event occurred affecting that area. Therefore, when monitoring a community of people, large or small, normal cold/flu epidemics, which take time to develop, can be observed and factored-out when determining the possibility of a bioterrorism event. On the other hand, an important part of this invention includes the early warning system's ability to monitor cold/flu epidemics.

FIGS. 4–8 provide a series of displays generated by the software of the present invention based on analysis of BMT data from a plurality of participants. FIG. 4 can be viewed along with the graph in FIG. 3, but the chart in FIG. 4 makes it easier to see when detection thresholds are triggered (note rows 7, 8 and 9 on days January 1–6). The chart also shows when the individual reports attending a gathering of more than 500 (a positive answer would appear on row 3 see also FIG. 2), experiencing symptoms of a cold/the flu or a sore throat (a positive answer would appear on row 2) and receiving a flu shot (a positive answer would appear on row 1).

Figure 6:
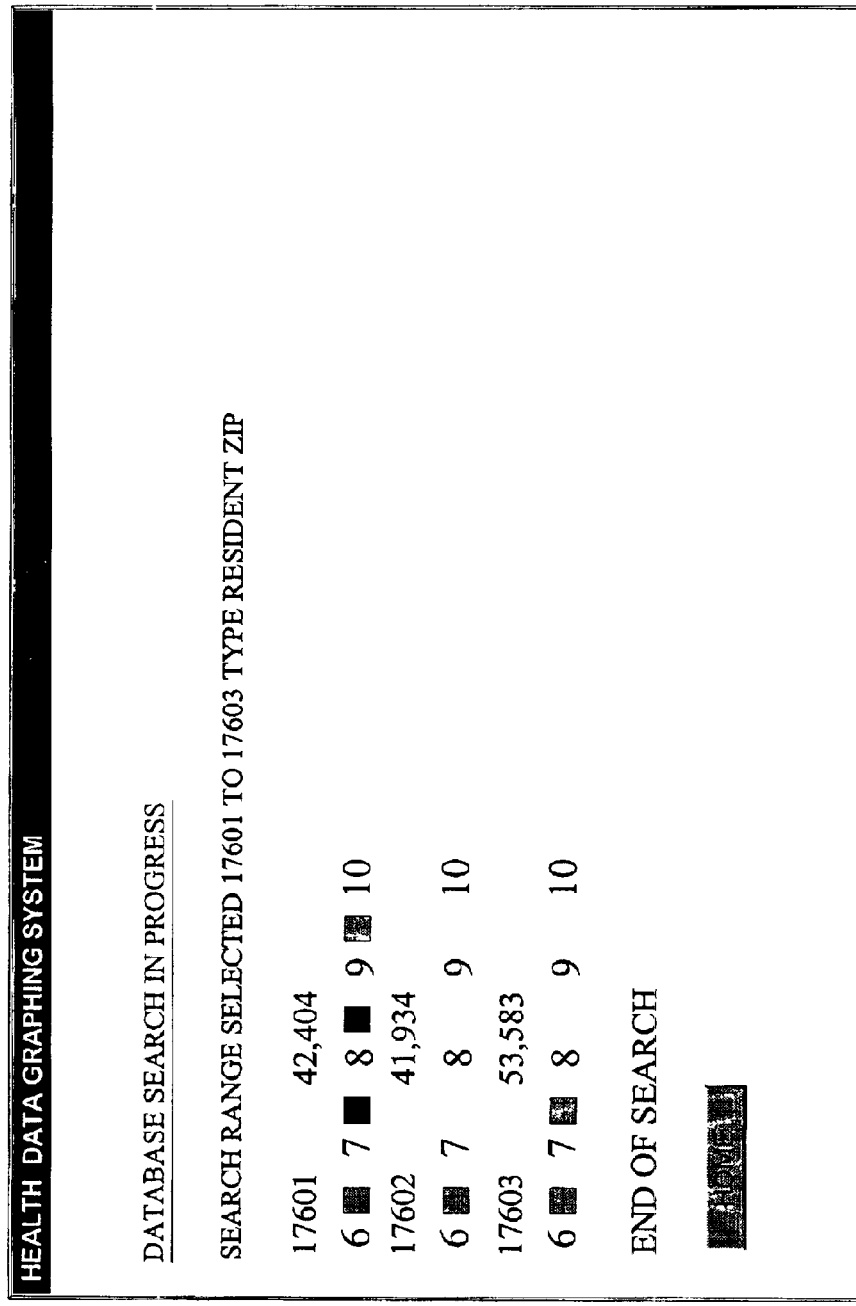
Figure 7:
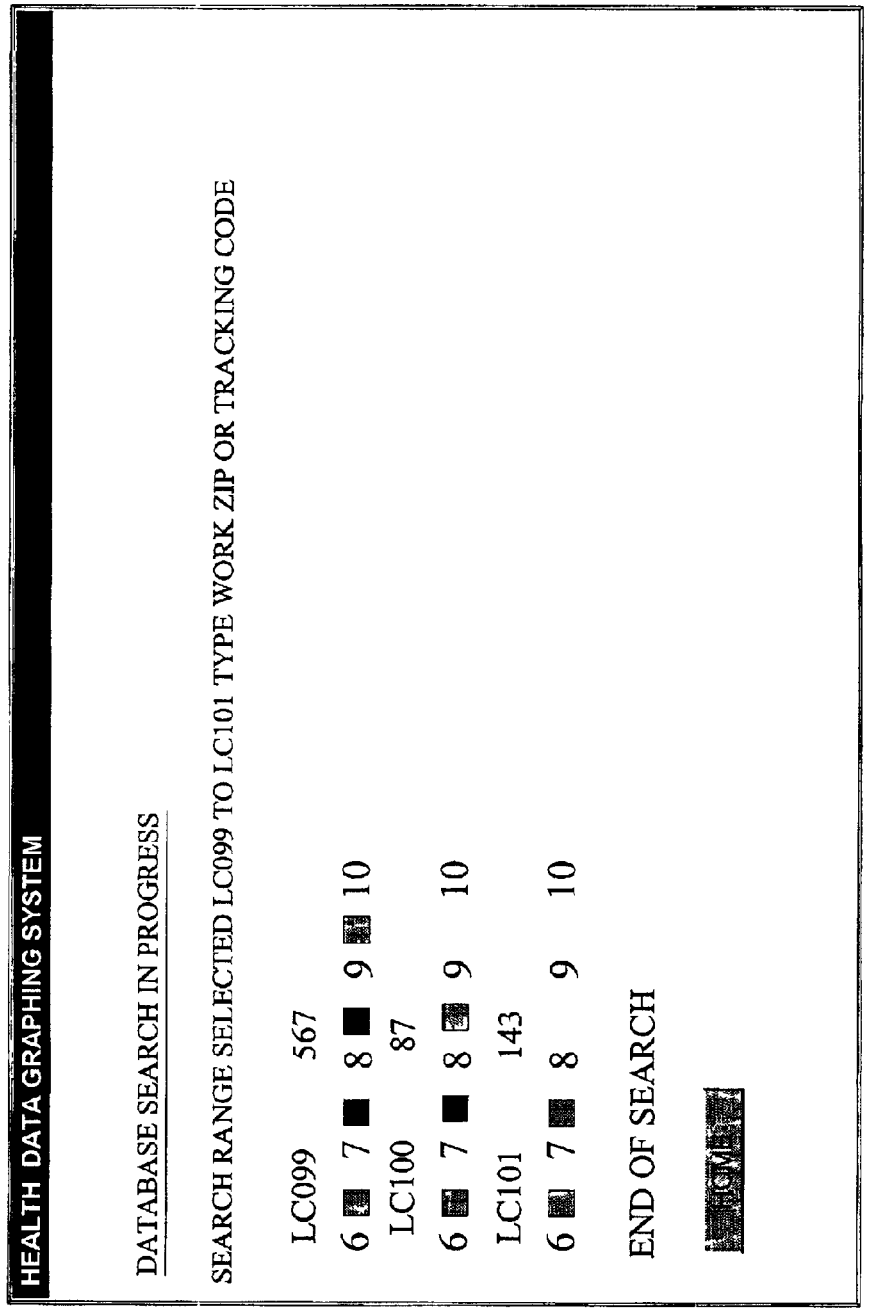
Figure 8:
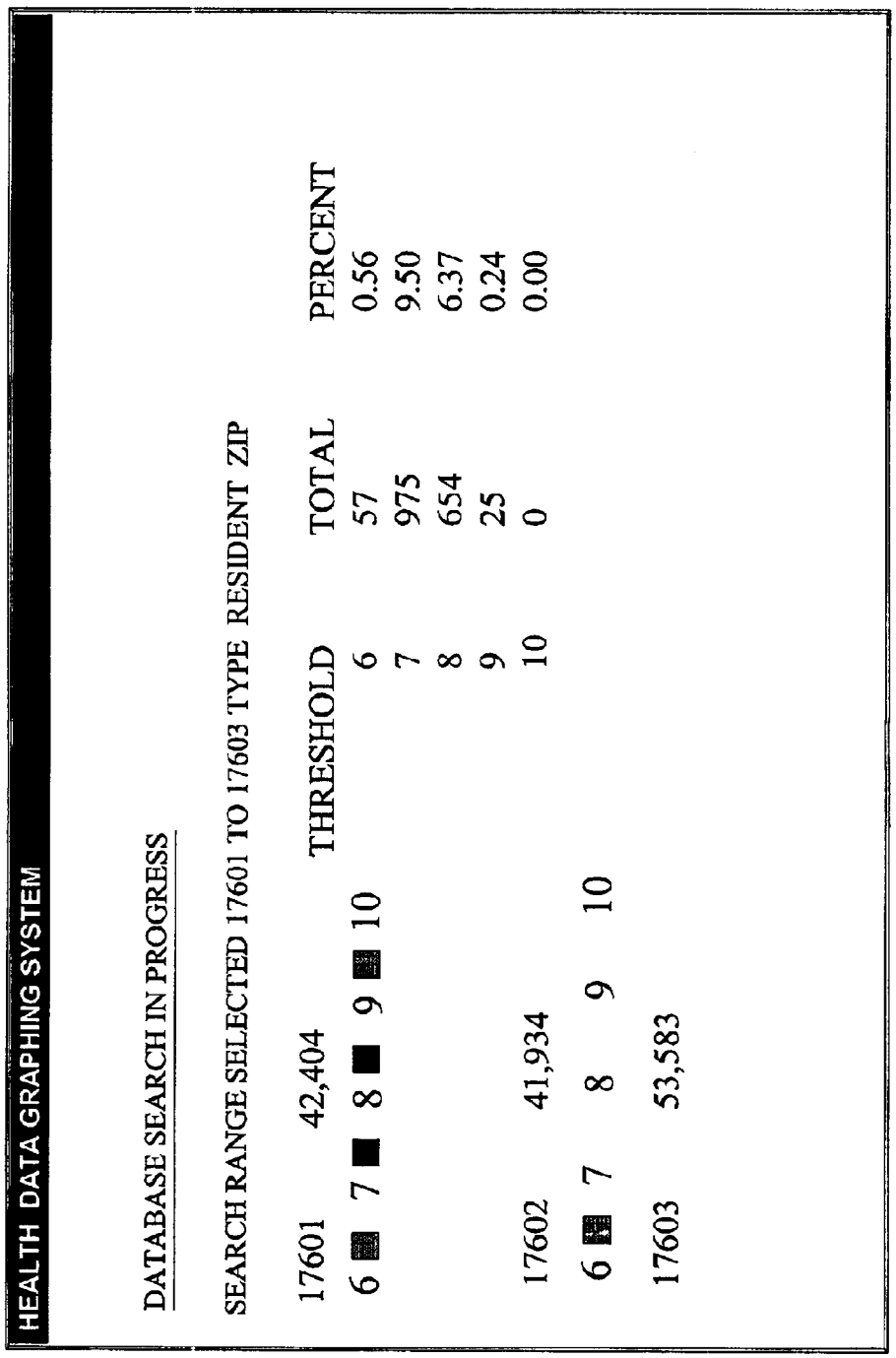

FIGS. 6–8 show the results of several types of database searches. In FIG. 6, a comparison of BMT data from three zip codes is depicted. The darkened squares following the numbers 7 and 8 represent a statistically significant number of individuals in the associated zip code having triggered detection thresholds 7 and 8. In an exemplary implementation of the invention, the squares that are filled indicate significant numbers of individuals in the associated zip code have triggered detection thresholds. Unfilled squares indicate some individuals in the associated zip code have triggered detection thresholds. Zip codes with no squares following their numbers have no individuals in the associated zip code that have triggered detection thresholds. The methodology can also be applied to specific locations within an area (FIG. 7), a public or private building of significance to the community or population at large. FIG. 8 shows a further way to analyze data within a zip code or other defined region by providing a tabular distribution vis-a-vis different threshold levels as well as by color-coding (not depicted) of the thresholds that have statistically significant percentages exceeding critical threshold values.

Figure 5:
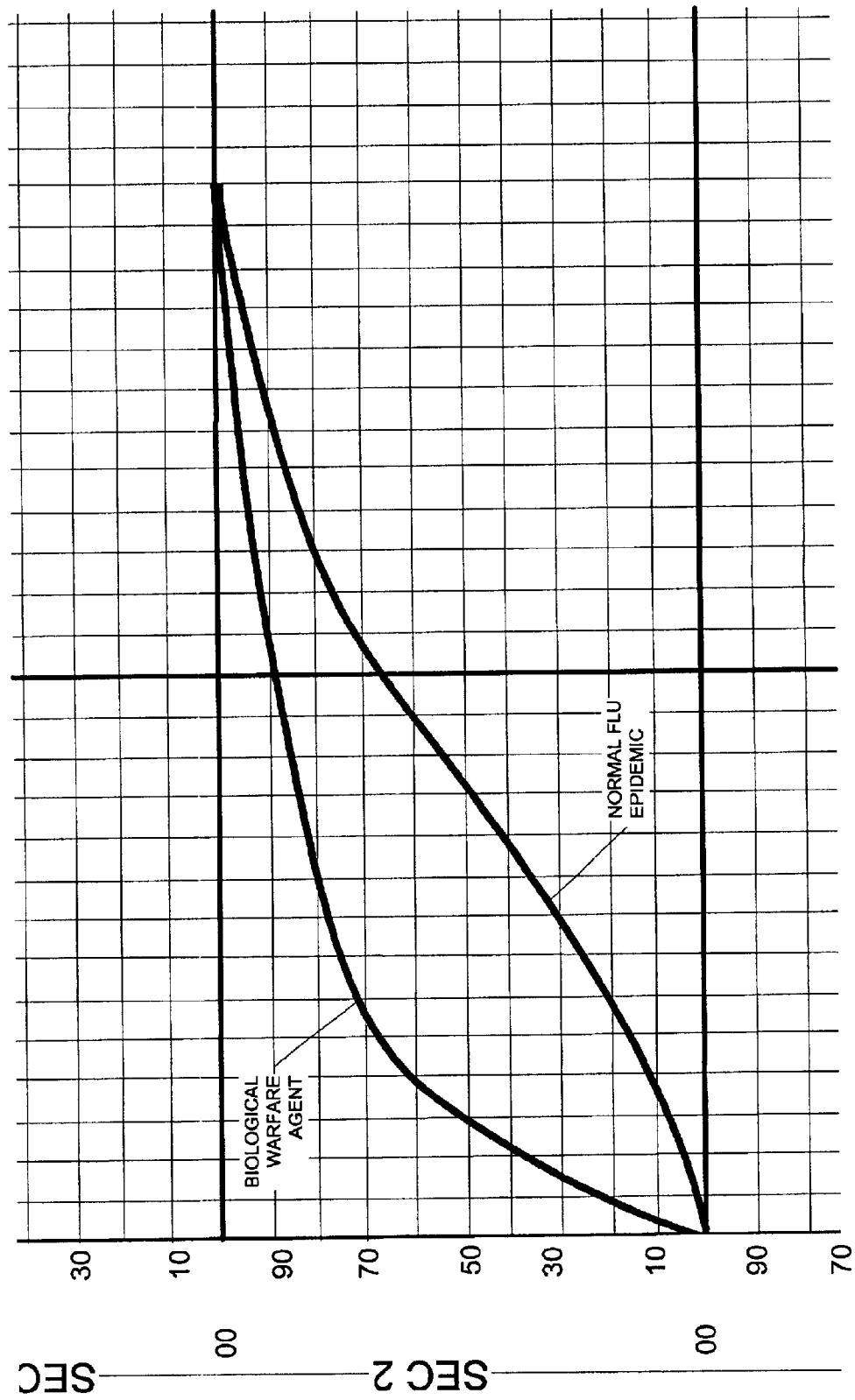

There is a second method to determine whether widespread $BMT^\Delta$ readings, that exceed detection thresholds, are the result of a normal occurring influenza epidemic or a bioterrorism event. The following method can be used to confirm decisions by health officials after immediate actions have been taken. Biological warfare agents introduced into a population will produce different curves than normal-occurring disease epidemics. The difference can be observed from one to three days after the event, in some cases even before individuals experience initial symptoms. FIG. 5 shows, in exemplary fashion, the rise in BMT average readings for an area attributable to a biological warfare agent as contrasted to a typical flu epidemic. The rise in BMT averages caused by a bioterrorism event will be far more rapid over the first few days following an infection.

On the other hand, since influenza presents initial symptoms very similar to many biological warfare agents, including anthrax and smallpox, individuals being monitored within given populations, the early warning system of this invention includes the following steps to protect individuals when their $BMT^\Delta$ readings exceed detection thresholds before the first flu-like symptoms are experienced:

1. receive from their physician or hospital emergency room personnel a throat-swab test for influenza (type A and B); and
2. if the throat swab test is negative, receive a blood test to look for other causal factors.

A recommended throat-swab test is the ZstatFlu test which is available from Zymetx, Inc. This is a 99% specific, rapid throat-swab test for types A and B influenza. Being able to rule out influenza as a causative agent enhances the capability to discover the true source of the pre-symptom, i.e., above detection threshold BMT readings, which could be the result of infection by a bioterrorism agent.

The above procedure as provided by this invention, i.e., monitoring an individual's BMT, observing $BMT^\Delta$ readings that exceed detection thresholds, receiving a throat-swab test for influenza, and, if negative, receiving a blood test for biological warfare agents, provides a means for the individual to take life-saving action in the event of an individual attack, such as through the postal system. The same procedure should be used by all individuals who are at particular risk, including first-responders (police, fire and emergency-response personnel).

The early warning detection system can also be used to identify potential infections that are not induced by a biological agent. For example, the methodology can be used to determine a possible infection of a large group before symptoms such as low grade fever set in. In a military setting, the temperature (not the BMT) of servicemen getting ready for deployment or a special mission could be recorded on a daily basis at the same time of day. If a sufficient number registered a temperature exceeding 99 degrees F., a conclusion can be quickly drawn that a health problem exists which can be treated before the problem spreads to others, thereby maintaining military readiness to deploy.

Although the description of the invention has disclosed the use of detection thresholds that, when exceeded, can be an indication of an infection by a biological agent, there are scenarios in which the BMT can drop below an established detection threshold and be used as an indication of infection. Therefore, the use of the word surpass in the claims below is intended to convey that a detection threshold is passed, whether exceeding a detection threshold set above the average BMT or falling below a detection threshold set below the average BMT.

The early warning detection system of the present invention can be realized in software or a combination of hardware and software. Any kind of computer system or other apparatus adapted for carrying out the methods described herein is suited. A typical combination of hardware and software in this context could be a web-based server computer with a computer program that, when loaded and executed, controls the web-based server computer such that it carries out the methods described herein. The early warning detection system can be embedded in a computer program product, which includes all the features enabling the implementation of the methods described herein, and which, when loaded in a computer system, is able to carry out these methods.

Additionally, the corresponding structures, materials, acts, and equivalents of all means plus function elements in any claims are intended to include any structure, material or acts for performing the functions in combination with other claim elements as specifically claimed.

Those skilled in the art will appreciate that many modifications to the exemplary embodiment of the present invention are possible without departing from the spirit and scope of the present invention. In addition, it is possible to use some of the features of the present invention without the corresponding use of the other features. Accordingly, the foregoing description of the exemplary embodiment is provided for the purpose of illustrating the principles of the present invention and not in imitation thereof since the scope of the present invention is defined solely by the appended claims.

What is claimed is:

1. A method for providing an early warning detection of a bioterrorism event, comprising the steps of:
   obtaining an individual's basal metabolic temperature;
   comparing the basal metabolic temperature to a detection threshold value; and
   identifying a basal metabolic temperature reading surpassing the detection threshold value that indicates a potential infection by a biological warfare agent.
2. The method for providing an early warning detection of a bioterrorism event of claim 1 wherein the detection threshold value is lower than a normally accepted temperature defined as a low-grade fever.

3. The method for providing an early warning detection of a bioterrorism event of claim 2 wherein the low-grade fever is defined as a temperature in a range of 100 degrees to 102 degrees Fahrenheit.

4. The method for providing an early warning detection of a bioterrorism event of claim 1 wherein the biological warfare agent is a Class A agent.

5. The method for providing an early warning detection of a bioterrorism event of claim 4 wherein the Class A agent is any one of anthrax, smallpox, pneumonic plague, Ebola hemorrhagic fever, Marburg hemorrhagic fever, Argentine hemorrhagic fever, and tularemia.

6. The method for providing an early warning detection of a bioterrorism event of claim 1 further comprising the step of determining a plurality of detection threshold values that are spaced apart by predetermined values to evaluate any identified potential infection by a biological warfare agent.

7. The method for providing an early warning detection of a bioterrorism event of claim 6 wherein at least one detection threshold value is lower than a normally accepted temperature defined as a low-grade fever.

8. The method for providing an early warning detection of a bioterrorism event of claim 6 wherein the plurality of detection threshold values is determined algorithmically based on an individual's normal cyclical changes in basal metabolic temperature.

9. The method for providing an early warning detection of a bioterrorism event of claim 6 wherein the plurality of detection threshold values is fixed.

10. The method for providing an early warning detection of a bioterrorism event of claim 1 wherein the detection threshold value is determined algorithmically based on an individual's normal cyclical changes in basal metabolic temperature.

11. A method for providing an early warning detection of a bioterrorism event, comprising the steps of:
obtaining an individual's basal metabolic temperature;
establishing a plurality of detection threshold values that are spaced apart by predetermined values, with at least one detection threshold value below a normally accepted temperature range defined as low-grade fever;
comparing the individual's basal metabolic temperature to the plurality of detection threshold values; and
identifying and evaluating a basal metabolic temperature reading surpassing at least one detection threshold that would indicate a potential infection by a biological warfare agent.

12. The method for providing an early warning detection of a bioterrorism event of claim 11 further comprising the step of determining the plurality of detection threshold values algorithmically based on an individual's normal cyclical changes in basal metabolic temperature.

13. The method for providing an early warning detection of a bioterrorism event of claim 11 wherein the low-grade fever is defined as a temperature in a range of 100 degrees to 102 degrees Fahrenheit.

14. The method for providing an early warning detection of a bioterrorism event of claim 11 wherein the biological warfare agent is a Class A agent.

15. The method for providing an early warning detection of a bioterrorism event of claim 14 wherein the Class A agent is any one of anthrax, smallpox, pneumonic plague, Ebola hemorrhagic fever, Marburg hemorrhagic fever, Argentine hemorrhagic fever, and tularemia.

16. A method for providing an early warning detection of a bioterrorism event in a community, comprising the steps of:
obtaining a basal metabolic temperature for each participant in a plurality of participants representing a sample of the community;
comparing each participant's basal metabolic temperature to a corresponding detection threshold value for the participant; and
identifying and evaluating a community-wide potential infection by a biological warfare agent based upon the number of participants having a basal metabolic temperature surpassing the participant's corresponding detection threshold value.

17. The method for providing an early warning detection of a bioterrorism event in a community of claim 16 wherein the sample of participants of the community is of a statistically significant size.

18. The method for providing an early warning detection of a bioterrorism event in a community of claim 16 further comprising the step of determining a plurality of detection threshold values for each participant that are spaced apart by predetermined values to evaluate the participant's potential infection by a biological warfare agent.

19. The method for providing an early warning detection of a bioterrorism event in a community of claim 18 further comprising the step of determining the plurality of detection threshold values for each participant algorithmically based on the participant's normal cyclical changes in basal metabolic temperature.

20. The method for providing an early warning detection of a bioterrorism event in a community of claim 19 wherein an algorithm for determining the plurality of detection threshold values includes averaging the basal metabolic temperature of each participant over a time period to establish a first detection threshold spaced apart from the average basal metabolic temperature by a predetermined value.

21. The method for providing an early warning detection of a bioterrorism event in a community of claim 20 wherein the period of time is approximately thirty days.

22. The method for providing an early warning detection of a bioterrorism event in a community of claim 20 further comprising an algorithm for determining an additional detection threshold value including the steps of:
averaging the basal metabolic temperature of each participant over a time period of approximately 30 days;
averaging the basal metabolic temperatures for each participant that are below the average basal metabolic temperature;
averaging the basal metabolic temperatures for each participant that are above the average basal metabolic temperature; and
establishing a detection threshold value that is spaced apart from the average basal metabolic temperature by a predetermined value when the participant's basal metabolic temperature is below the average basal metabolic temperature and spaced apart from the above-average basal metabolic temperature when the participant's basal metabolic temperature is above the average basal metabolic temperature to provide a detection threshold value that is responsive to a participant's cyclical basal metabolic temperatures.

23. The method for providing an early warning detection of a bioterrorism event in a community of claim 20 further comprising an algorithm for determining an additional detection threshold value including the steps of:
averaging the basal metabolic temperature of each participant over a first time period of approximately 30 days;
averaging the basal metabolic temperatures for each participant that are below the average metabolic temperature;

averaging the basal metabolic temperatures for each participant that are above the average basal metabolic temperature;

determining a switchover point, after a second time period of approximately 30 days, at which the participant's basal metabolic temperature typically changes from basal metabolic temperature readings below the average basal metabolic temperature to basal metabolic temperature readings above the average basal metabolic temperature;

developing an average baseline basal metabolic temperature for each day of a participant's cycle over a plurality of time periods;

establishing a detection threshold value that is spaced apart from the participant's baseline basal metabolic temperatures by a predetermined value to provide a detection threshold value that is responsive to a participant's cyclical basal metabolic temperatures.

24. The method for providing an early warning detection of a bioterrorism event in a community of claim 19 wherein the plurality of detection thresholds are fixed values.

25. The method for providing an early warning detection of a bioterrorism event in a community of claim 16 further comprising the step of comparing the average basal metabolic temperature readings of a plurality of participants in a plurality of communities to determine if the plurality of participants in any community has experienced a sudden increase in participant's basal metabolic temperature readings that surpass the participant's threshold detection values.

26. The method for providing an early warning detection of a bioterrorism event in a community of claim 25 wherein the plurality of participants includes all participants of the community.

27. The method for providing an early warning detection of a bioterrorism event in a community of claim 25 wherein the plurality of participants includes a statistically significant number of participants of the community.

28. The method for providing an early warning detection of a bioterrorism event in a community of claim 25 where each of the plurality of communities are drawn from a different geographical region.

29. The method for providing an early warning detection of a bioterrorism event in a community of claim 28 wherein each geographical region has a distinct zip code.

30. The method for providing an early warning detection of a bioterrorism event in a community of claim 16 further comprising the step of comparing the average basal metabolic temperature readings of a plurality of participants in a plurality of communities to determine a percentage increase in participants' basal metabolic temperature readings that exceed the participants' threshold detection values for the plurality of participants in each community.

31. The method for providing an early warning detection of a bioterrorism event in a community of claim 16 further comprising the step of comparing graphically, over a period of time, average basal metabolic temperature readings of a plurality of participants in the community with basal metabolic temperature readings that result during a typical influenza epidemic as an indication of a likelihood that a bioterrorism event has occurred.

32. A method for providing an early warning detection of a bioterrorism attack on an individual, comprising the steps of:

obtaining a basal metabolic temperature for the individual over a period of time;

comparing the individual's basal metabolic temperature to a detection threshold value to evaluate the individual's risk of having been infected by a biological warfare agent; and determining if the individual actually has been infected by the biological warfare agent.

33. The method for providing an early warning detection of a bioterrorism event in an individual of claim 32 wherein the step of determining actual infection of the individual comprises:

receiving a throat-swab test for influenza; and if the test for influenza is negative, obtaining a blood sample from the individual and testing the blood sample for a suspected biological warfare agent.

34. The method for providing an early warning detection of a bioterrorism event in an individual of claim 32 wherein the detection threshold value is determined algorithmically based on an individual's normal cyclical changes in basal metabolic temperature.

35. The method for providing an early warning detection of a bioterrorism event in an individual of claim 32 further comprising the step of determining a plurality of detection threshold values that are spaced apart by predetermined values to evaluate any identified potential infection by a biological warfare agent.

36. The method for providing an early warning detection of a bioterrorism event in an individual of claim 35 wherein the plurality of detection threshold values is determined algorithmically based on an individual's normal cyclical changes in basal metabolic temperature.

37. A computer readable medium containing a computer program product for providing an early warning detection of a bioterrorism event, the computer program product comprising:

program instructions that obtain an individual's basal metabolic temperature;

program instructions that compare the basal metabolic temperature to a detection threshold value; and program instructions that identify a basal metabolic temperature reading that indicates a potential infection by a biological warfare agent.

38. The computer program product for providing an early warning detection of a bioterrorism event of claim 37 wherein the detection threshold value is lower than a normally accepted temperature defined as a low-grade fever.

39. The computer program product for providing an early warning detection of a bioterrorism event of claim 37 wherein the low-grade fever is defined as a temperature in a range of 100 degrees to 102 degrees Fahrenheit.

40. The computer program product for providing an early warning detection of a bioterrorism event of claim 37 wherein the biological warfare agent is a Class A agent.

41. The computer program product for providing an early warning detection of a bioterrorism event of claim 40 wherein the Class A agent is any one of anthrax, smallpox, pneumonic plague, Ebola hemorrhagic fever, Marburg hemorrhagic fever, Argentine hemorrhagic fever, and tularemia.

42. The computer program product for providing an early warning detection of a bioterrorism event of claim 37 further comprising program instructions that determine a plurality of detection threshold values that are spaced apart by predetermined values to evaluate any identified potential infection by a biological warfare agent.

43. The computer program product for providing an early warning detection of a bioterrorism event of claim 42 wherein at least one detection threshold value is lower than a normally accepted temperature defined as a low-grade fever.

44. The computer program product for providing an early warning detection of a bioterrorism event of claim 42 further comprising program instructions that determine an additional detection threshold value based on an individual's normal cyclical changes in basal metabolic temperature.

45. The computer program product for providing an early warning detection of a bioterrorism event of claim 37 further comprising program instructions that determine an additional detection threshold value based on an individual's normal cyclical changes in basal metabolic temperature.

46. A computer readable medium containing a computer program product for providing an early warning detection of a bioterrorism event, the computer program product comprising:
   program instructions that obtain an individual's basal metabolic temperature;
   program instructions that establish a plurality of detection threshold values that are spaced apart by predetermined values, with at least one detection threshold value below a normally accepted temperature range defined as low-grade fever;
   program instructions that compare the individual's basal metabolic temperature to the plurality of detection threshold values; and
   program instructions that identify and evaluate a basal metabolic temperature reading that would indicate a potential infection by a biological warfare agent.

47. The computer program product for providing an early warning detection of a bioterrorism event of claim 46 further comprising program instructions that determine an additional detection threshold value based on an individual's normal cyclical changes in basal metabolic temperature.

48. The computer program product for providing an early warning detection of a bioterrorism event in a community of claim 47 further comprising program instructions that determine a plurality of detection threshold values for each participant that are spaced apart by predetermined values to evaluate the participant's potential infection by a biological warfare agent.

49. The computer program product for providing an early warning detection of a bioterrorism event in a community of claim 48 further comprising program instructions that determine an additional detection threshold value for each participant based on the participant's normal cyclical changes in basal metabolic temperature.

50. The computer program product for providing an early warning detection of a bioterrorism event in a community of claim 49 wherein the program instructions that determine the plurality of detection threshold values include program instructions that average the basal metabolic temperature of each participant over a time period to establish a detection threshold spaced apart from the average basal metabolic temperature by a predetermined value.

51. The computer program product for providing an early warning detection of a bioterrorism event in a community of claim 50 wherein the period of time is approximately thirty days.

52. The computer program product for providing an early warning detection of a bioterrorism event in a community of claim 50 wherein the program instructions that determine an additional detection threshold value include:
   program instructions that average the basal metabolic temperature of each participant over a time period of approximately 30 days;
   program instructions that average the basal metabolic temperatures for each participant that are below the average basal metabolic temperature;
   program instructions that average the basal metabolic temperatures for each participant that are above the average basal metabolic temperature; and
   program instructions that establish a detection threshold value that is spaced apart from the below average basal metabolic temperature by a predetermined value when the participant's basal metabolic temperature is below the average basal metabolic temperature, and spaced apart from the above average basal metabolic temperature when the participant's basal metabolic temperature is above the average basal metabolic temperature to provide a detection threshold value that is responsive to a participant's cyclical basal metabolic temperatures.

53. The computer program product for providing an early warning detection of a bioterrorism event in a community of claim 50 wherein the program instructions that determine an additional detection threshold value include:
   program instructions that average the basal metabolic temperature of each participant over a first time period of approximately 30 days;
   program instructions that average the basal metabolic temperature for each participant that are below the average basal metabolic temperature;
   program instructions that average the basal metabolic temperature for each participant that are above the average basal metabolic temperature;
   program instructions that determine a switchover point, after a second time period of approximately 30 days, at which the participant's basal metabolic temperature typically changes from basal metabolic temperature readings below the average basal metabolic temperature to basal metabolic temperature readings above the average metabolic temperature;
   program instructions that develop an average baseline basal metabolic temperature for each day of the participant's cycle over a plurality of time periods; and
   program instructions that establish a detection threshold value that is spaced apart from the participant's baseline basal metabolic temperatures by a predetermined value to provide a detection threshold value that is responsive to a participant's cyclical basal metabolic temperatures.

54. The computer program product for providing an early warning detection of a bioterrorism event in a community of claim 53 further comprising program instructions that compare the average basal metabolic temperature readings of a plurality of participants in a plurality of communities to determine if the plurality of participants in any community has experienced a sudden increase in participant's basal metabolic temperature readings that surpass the participant's threshold detection values.

55. The computer program product for providing an early warning detection of a bioterrorism event in a community of claim 54 wherein the plurality of participants includes all participants of the community.

56. The computer program product for providing an early warning detection of a bioterrorism event in a community of claim 54 wherein the plurality of participants includes a statistically significant number of participants of the community.

57. The computer program product for providing an early warning detection of a bioterrorism event in a community of claim 54 where each of the plurality of communities are drawn from a different geographical region.

58. The computer program product for providing an early warning detection of a bioterrorism event in a community of claim 57 wherein each geographical region has a distinct zip code.

59. The computer program product for providing an early warning detection of a bioterrorism event in a community of claim 53 further comprising program instructions that compare the average basal metabolic temperature reading of a plurality of participants in a plurality of communities to determine a percentage increase in participants' basal metabolic temperature readings that surpass the participants' threshold detection values for the plurality of participants in the community.

60. The computer program product for providing an early warning detection of a bioterrorism event in a community of claim 53 further comprising program instructions that compare graphically, over a period of time, average basal metabolic temperature readings of a plurality of participants in the community with basal metabolic temperature readings that result during a typical influenza epidemic as an indication of a likelihood that a bioterrorism event has occurred.

61. The computer program product for providing an early warning detection of a bioterrorism event of claim 46 wherein the low-grade fever is defined as a temperature in a range of 100 degrees to 102 degrees Fahrenheit.

62. The computer program product for providing an early warning detection of a bioterrorism event of claim 46 wherein the biological warfare agent is a Class A agent.

63. The computer program product for providing an early warning detection of a bioterrorism event of claim 62 wherein the Class A agent is any one of anthrax, smallpox, pneumonic plague, Ebola hemorrhagic fever, Marburg hemorrhagic fever, Argentine hemorrhagic fever, and tularemia.

64. A computer readable medium containing a computer program product for providing an early warning detection of a bioterrorism event in a community, the computer program product comprising:
   program instructions that input a basal metabolic temperature for each participant in a plurality of participants representing a sample of the community;
   program instructions that compare each participant's basal metabolic temperature to a corresponding detection threshold value for the participant that is below a normally accepted temperature defined as a low-grade fever; and
   program instructions that identify and evaluate a community-wide potential infection by a biological warfare agent.

65. The computer program product for providing an early warning detection of a bioterrorism event in a community of claim 64 wherein the sample of participants of the community is of a statistically significant size.

66. A system for providing an early warning detection of a bioterrorism event, comprising:
   a telephone server for forwarding basal metabolic temperatures received from a plurality of individuals;
   a database server for receiving the basal metabolic temperatures and operative with a database to store the basal metabolic temperatures in a record for each individual; and
   a website server for enabling access to the stored records by an early warning detection system administrator.

67. The system for providing an early warning detection of a bioterrorism event of claim 66 further comprising:
   a thermometer for determining an individual's basal metabolic temperature and including a transmitter for automatically transmitting the basal metabolic temperature; and
   a receiver for receiving the basal metabolic temperature from a plurality of individuals.

68. The system for providing an early warning detection of a bioterrorism event of claim 67 wherein the transmitter transmits the basal metabolic temperature via wireless communications.

69. The system for providing an early warning detection of a bioterrorism event of claim 66 further comprising a computer program operating on the website server and comprising:
   an input component for reading an individual's stored basal metabolic temperatures;
   an analysis component for establishing a detection threshold value for the individual and comparing a new basal metabolic temperature to the detection threshold value; and
   an identification component for identifying a new basal metabolic temperature reading that exceeds the threshold detection value indicating a potential infection by a biological warfare agent.

70. The system for providing an early warning detection of a bioterrorism event of claim 69 wherein the biological warfare agent is a Class A agent.

71. The system for providing an early warning detection of a bioterrorism event of claim 70 wherein a first module averages the stored basal metabolic temperatures for the individual and establishes a detection threshold spaced apart from the average basal metabolic temperature by a predetermined value.

72. The system for providing an early warning detection of a bioterrorism event of claim 71 wherein a second module averages the basal metabolic temperatures that are above the average basal metabolic temperature, averages the basal metabolic temperatures that are below the average basal metabolic temperature, and determines a threshold detection value that is spaced apart from the average metabolic temperature by a predetermined value corresponding to the above average value and below average value, respectively.

73. The system for providing an early warning detection of a bioterrorism event of claim 72 wherein a third module determines a switchover point, after a plurality of time periods of approximately 30 days, at which the individual's basal metabolic temperature typically changes from basal metabolic temperature readings below the average basal metabolic temperature to basal metabolic temperature readings above the average basal metabolic temperature; develops an average baseline basal metabolic temperature for each day of the individual's cycle over the plurality of time periods; and establishes a detection threshold value that is spaced apart from the individual's baseline basal metabolic temperatures by a predetermined value to provide a detection threshold value that is responsive to the individual's cyclical basal metabolic temperatures.

74. The system for providing an early warning detection of a bioterrorism event of claim 69 wherein the analysis component comprises a plurality of modules for establishing threshold detection values that are based on an individual's cyclical changes in basal metabolic temperature.

75. The system for providing an early warning detection of a bioterrorism event of claim 66 further comprising:
   a thermometer for determining an individual's basal metabolic temperature; and
   a communications device for sending the basal metabolic temperature to a server device.

76. The system for providing an early warning detection of a bioterrorism event of claim 75 wherein the communication device is any one of a telephone, a personal computer, a personal digital assistant, a laptop computer, a handheld device, and a workstation.

77. The system for providing an early warning detection of a bioterrorism event of claim 75 wherein the server device is a telephone server connected to multiple incoming telephone lines.

78. The system for providing an early warning detection of a bioterrorism event of claim 75 wherein the server device is a website server that communicates with the communication device over a public network.

79. The system for providing an early warning detection of a bioterrorism event of claim 78 wherein the public network is the Internet.

80. The system for providing an early warning detection of a bioterrorism event of claim 75 wherein the server device is a website server that communicates with the communication device over a private network.

81. A method for providing an early warning detection of a potential infection, comprising the steps of:

obtaining an individual's basal metabolic temperature;

comparing the basal metabolic temperature to a detection threshold value; and identifying a basal metabolic temperature reading surpassing the detection threshold value that indicates a potential infection.

82. The method for providing an early warning detection of claim 81 wherein the potential infection is caused by a biological warfare agent.

83. The method for providing an early warning detection of claim 81 wherein the potential infection is caused by an influenza virus.

84. A method for providing an early warning detection of a potential infection in a community, comprising the steps of:

obtaining a temperature reading for each participant in a plurality of participants that are members of the community;

comparing each participant's temperature to a detection threshold value; and identifying and evaluating a community-wide potential infection based upon the number of participants having a temperature surpassing the detection threshold value.

85. The method for providing an early warning detection of a potential infection in a community of claim 84 wherein the plurality of participants from the community is of a statistically significant size.

86. The method for providing an early warning detection of a potential infection in a community of claim 85, further comprising the step of determining a plurality of detection threshold values that are spaced apart by predetermined values to evaluate each participant's potential infection.

* * * * *